US005170798A

United States Patent [19]
Riker

[11] Patent Number: 5,170,798
[45] Date of Patent: * Dec. 15, 1992

[54] PULMONARY FUNCTION TESTER

[75] Inventor: Douglas M. Riker, Brookline, Mass.

[73] Assignee: Sherwood Medical Company, St. Louis, Mo.

[*] Notice: The portion of the term of this patent subsequent to Oct. 22, 2008 has been disclaimed.

[21] Appl. No.: 780,496

[22] Filed: Oct. 22, 1991

Related U.S. Application Data

[63] Continuation of Ser. No. 512,052, Apr. 12, 1990, Pat. No. 5,058,601, which is a continuation of Ser. No. 341,275, Apr. 19, 1989, abandoned, which is a continuation of Ser. No. 154,793, Feb. 10, 1988, abandoned.

[51] Int. Cl.$^5$ .............................................. A61B 5/087
[52] U.S. Cl. .................................. 128/725; 364/413.03
[58] Field of Search ............................... 128/724-726; 364/413.03

[56] References Cited

U.S. PATENT DOCUMENTS

| | | | |
|---|---|---|---|
| 3,621,835 | 11/1971 | Suzuki et al. | 128/725 |
| 3,797,479 | 3/1974 | Graham | 128/725 |
| 3,910,261 | 10/1975 | Ragsdale et al. | 128/719 |
| 3,924,612 | 12/1975 | Dempster et al. | 128/725 |
| 3,946,729 | 3/1976 | Hanna . | |
| 4,258,718 | 3/1981 | Goldman | 128/725 |
| 4,736,750 | 4/1988 | Valdespino et al. | 128/725 |
| 4,765,342 | 8/1988 | Urman et al. | 128/725 |
| 5,058,601 | 10/1991 | Riker | 128/725 |

FOREIGN PATENT DOCUMENTS

| | | | |
|---|---|---|---|
| 8401704 | 5/1984 | PCT Int'l Appl. | 128/725 |
| 8501867 | 5/1985 | PCT Int'l Appl. | 128/725 |
| 2133157 | 7/1984 | United Kingdom . | |

OTHER PUBLICATIONS

Gulesian, IEEE Trans Bio-Med Engr, vol. BME-18, No. 5 Sep. 1971, pp. 378-379.
Am. Rev. Respir. Dis. 1987; 136; 1285-1295, "Standardization of Spirometry-1987 Update".
Hess et al, "An Evaluation of the Respiradyne II Spirometer", Respiratory Care; vol. 32, No. 12, pp. 1123-1130, Dec. 1987.
Zimnicki et al., Evaluation of the Respiradyne Pulmonary Function Monitor, Respiratory Care; vol. 32, No. 4, pp. 261-267, Apr. 1987.
Nelson et al., Performance Evaluation of Contemporary Spirometers, Chest/97/2; Feb. 1990, pp. 288-297.

Primary Examiner—Lee S. Cohen
Attorney, Agent, or Firm—Andrew J. Beck; Montgomery W. Smith; Curtis D. Kinghorn

[57] ABSTRACT

An improved pulmonary function tester provides for dynamic calibration during patient testing of various modes such as Forced Vital Capacity (FVC), Resting Ventilation (RV), Negative Inspiratory Force (NIF) and Maximum Voluntary Ventilation (MVV). The improved tester senses the ambient atmospheric pressure prior to and after sensing the pressure created by a patient's pulmonary function. The pressure created by a patient's pulmonary function is calibrated in view of the difference between the ambient atmospheric pressure sensed prior to and after sensing the pressure created by a patient's pulmonary function. In the preferred embodiment, during testing in the modes, when the airflow from a patient's pulmonary tract is detected to be below a selected value indicating minimal or substantially no airflow, a pressure transducer which is used to detect mouthpiece airflow is vented to the ambient atmosphere, and data representing the output of the pressure transducer are taken and stored for calibration of later readings during testing.

24 Claims, 9 Drawing Sheets

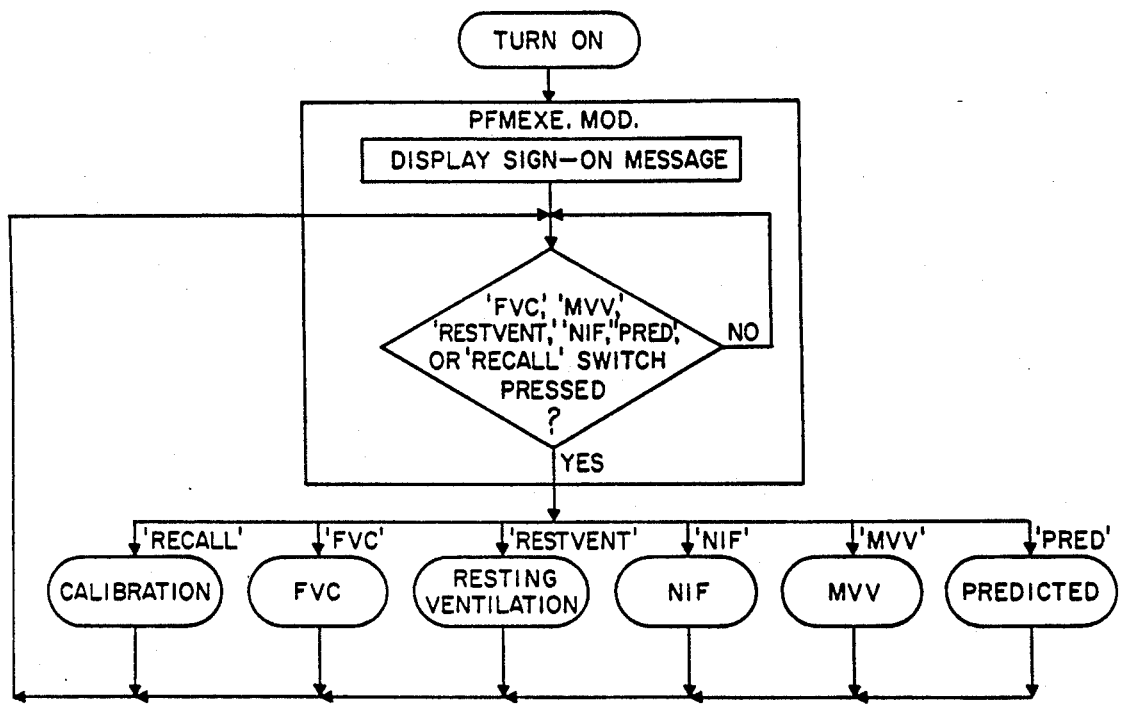
FIG. 5a
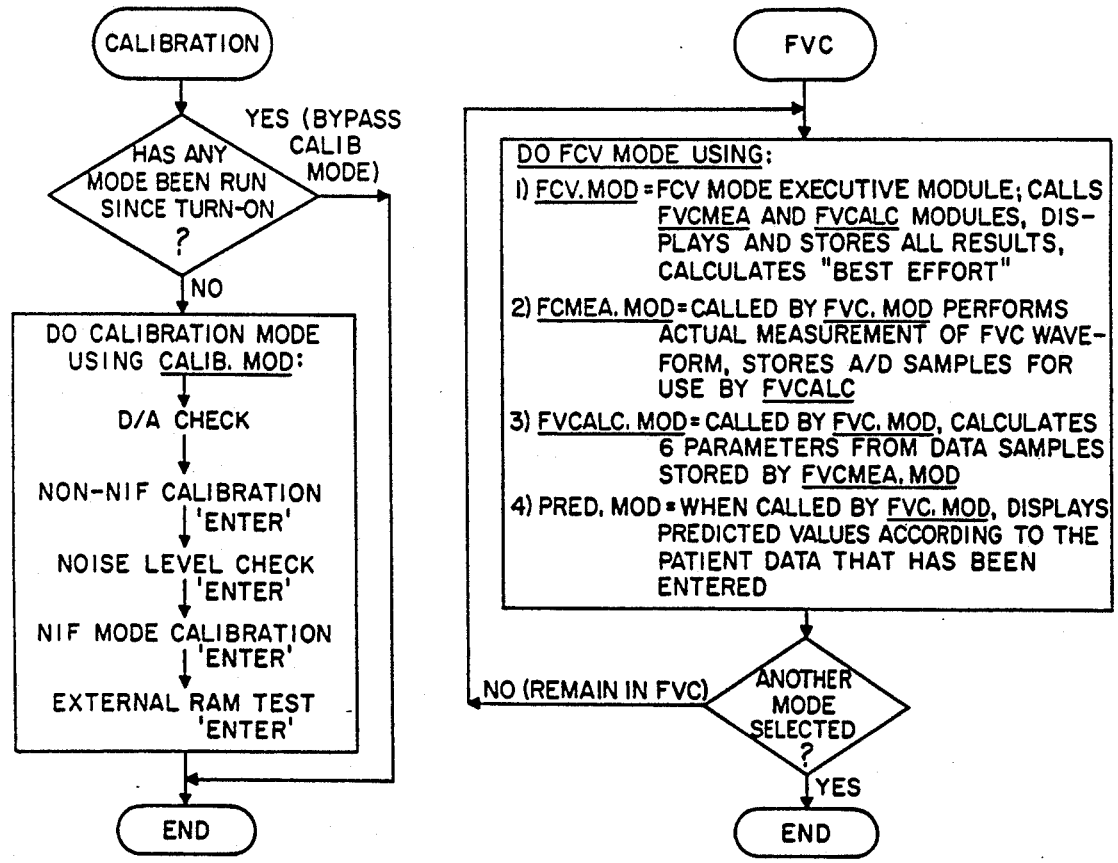
FIG. 5b
FIG. 5c

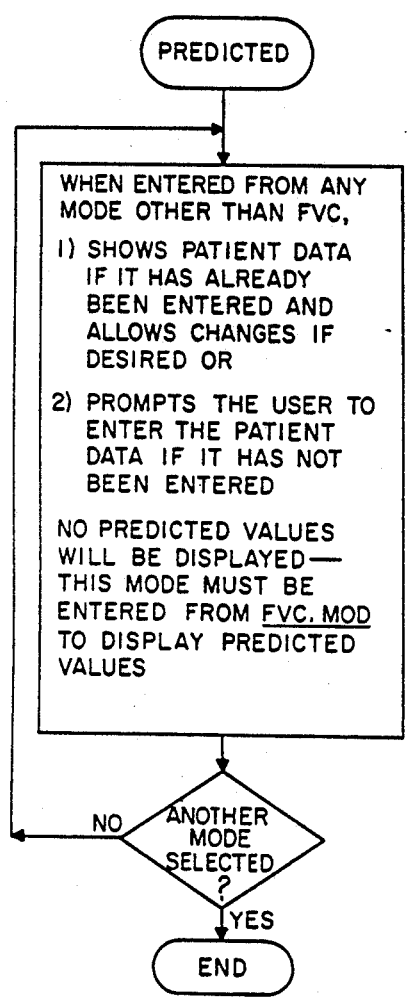
FIG. 5g
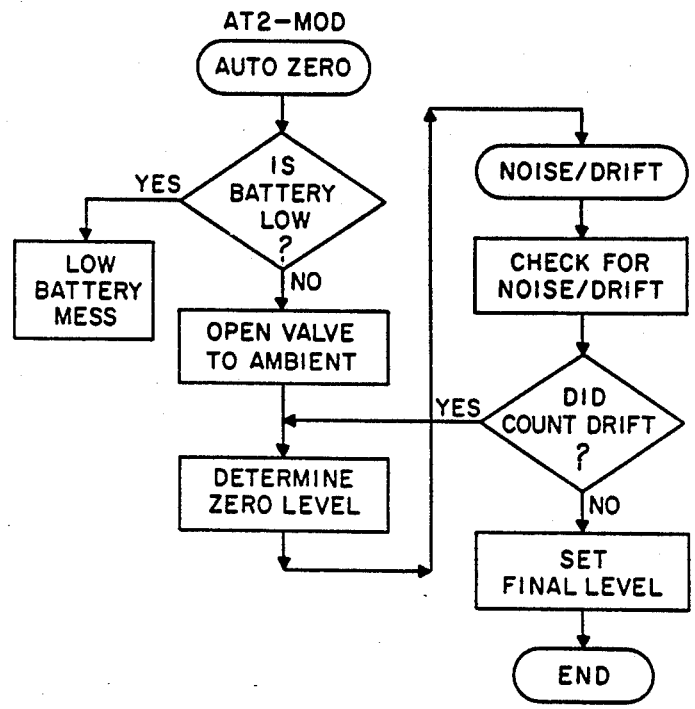
FIG. 5h
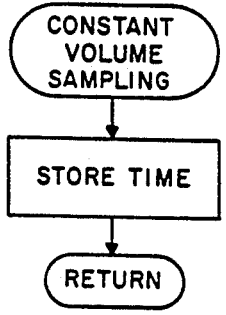
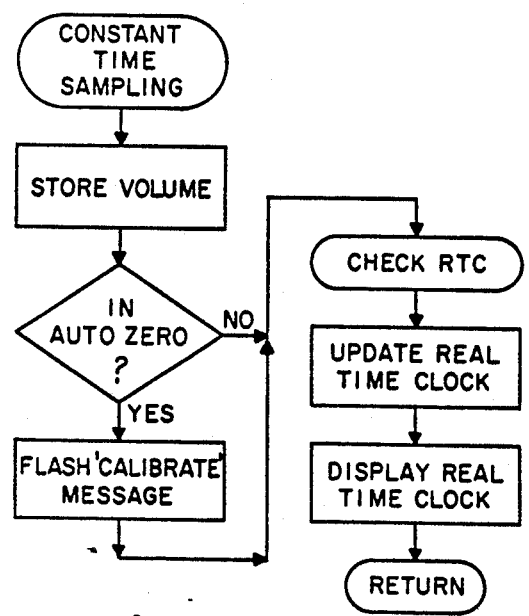
FIG. 5ℓ

PULMONARY FUNCTION TESTER

This application is a continuation of application Ser. No. 07/512,052, filed Apr. 12, 1990, now issued as U.S. Pat. No. 5,058,601 on Oct. 22, 1991, which is a continuation of application Ser. No. 07/341,275 filed Apr. 19, 1989, now abandoned, which is a continuation of application Ser. No. 07/154,793, filed Feb. 10, 1988, now abandoned.

This application makes reference to a certified copy of the appendix filed in the original application which is attached hereto. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention relates to pulmonary function testers and more particularly to spirometers which measure air entering and leaving the lungs during different breathing patterns.

2. Description of Related Art

Various types of techniques have been used to measure respiratory flow in pulmonary function testers. One such technique determines air flow and volume by measuring the pressure differential created by air flowing across a resistance in a tube. For clinical evaluation it is desirable that a device be capable of measuring air flow volume in the range of 12 milliliters/second (ml/sec) to 12 liters per second (1/sec), which is a range of 1,000-to-1. For example, for a pulmonary function tester using an orifice as a resistance element, the air flow to resistance differential has a square-law relationship. Therefore, it is necessary to measure pressure over a relatively large range. Furthermore, in clinical evaluation, it is necessary, according to ATS standards, for the pulmonary function tester to have a high accuracy on the order of 3%. Thus, clinical devices should not only be capable of measuring over a relatively large pressure range, but also provide accurate measurements.

Existing pulmonary testers often go out of calibration, i.e. their "zero level" shifts, resulting in inaccurate measurements. In one particular type of pulmonary function tester wherein a pressure transducer is used to detect pressure changes, the stability of the transducer output voltage at zero pressure input ("zero" or "zero level") becomes the most important performance characteristic, as either long term or short term drift adversely effects the operation and accuracy of the instrument. This is particularly so where the transducer manufacturer's zero drift specifications typically approach ⅓ of the maximum pressure which is created when the pulmonary function tester is in use. Thus, close attention to the zero level is important to achieving an overall 3% volume and flow measuring accuracy.

SUMMARY OF THE INVENTION

In accordance with the present invention, a pulmonary function tester is provided with means for dynamically calibrating the tester during tester use. The pulmonary function tester comprises a mouthpiece and conduit means having two ends, with one end connected to the mouthpiece and the other end connected to a transducer means, said transducer means sensing pressure in the conduit means indicative of airflow therethrough, and for producing an output signal indicative of the amount of pressure. Valve means are provided connected to the conduit means, for venting the transducer to atmosphere. Dynamic calibration means are provided for detecting when the pressure drops below a selected level during a selected portion of the flow-time curve, for opening the valve means for a time interval sufficient to obtain an accurate pressure reading when the valve means is opened, for storing zero level data representative of the transducer output signal when the valve means is opened, and for calibrating subsequent pressure readings of the transducer output using the zero level data.

The re-zeroing is particularly necessary for determination of "end-of-flow." The point in time at which "end-of-flow" occurs is critical in one calculated parameter, FEF25-75. If re-zeroing is not done, and the zero done, and the zero level shifted slightly during the maneuver, a false "end-of-flow" point could be detected.

The unit is relatively small in size and is portable so that it can be easily carried from bed to bed. The unit has a variety of measuring modes; including Forced Vital Capacity (FVC), Resting Ventilation (RV), Maximum Voluntary Ventilation (MVV) and Negative Inspiratory Force (NIF) modes. Storage means are provided for storing data gathered. For example, in the FVC mode, data from up to 15 FVC maneuvers can be stored for later recall.

Other advantages and objects of the invention will become apparent when considering the following description of a preferred embodiment, the accompanying claims and the drawings.

BRIEF DESCRIPTION OF THE DRAWINGS

FIGS. 5a through 5l are flowcharts of the control program according to the invention.

DETAILED DESCRIPTION OF THE PREFERRED EMBODIMENT

Figure 1:
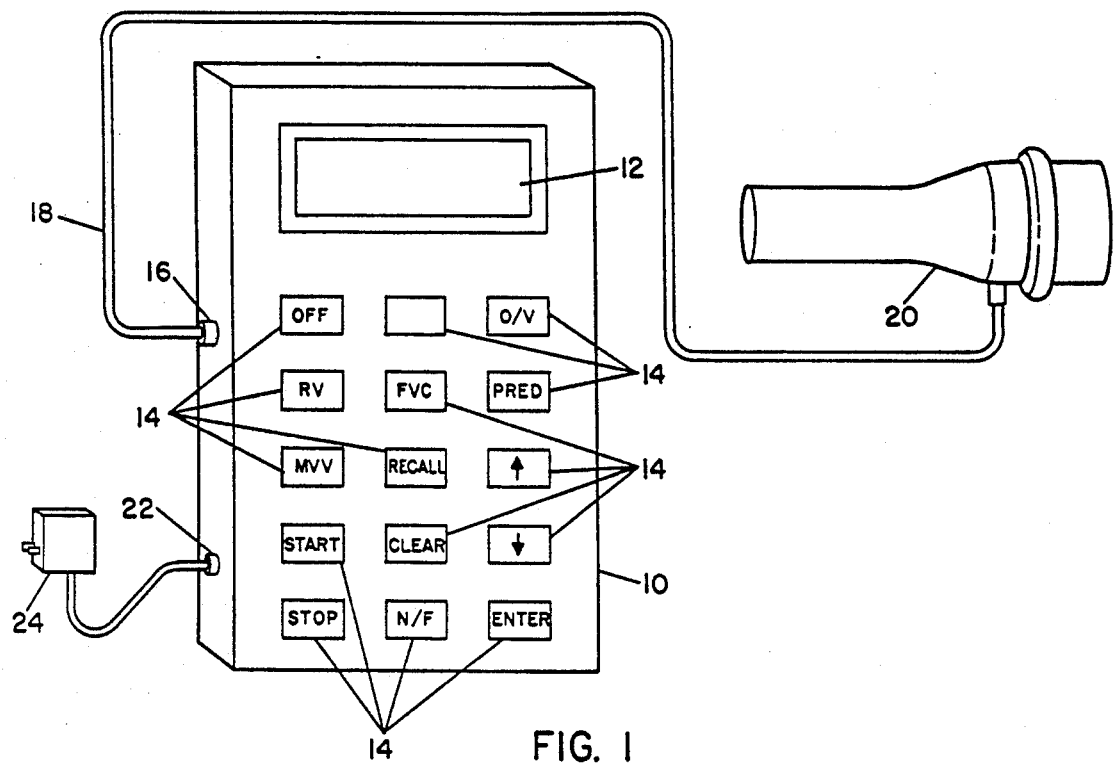
FIG. 1 is a perspective view of a pulmonary function tester according to the invention, including a mouthpiece, conduit and housing for the circuitry and other components.

Referring to FIG. 1, a pulmonary function tester according to the invention comprises a housing 10 having an LCD display 12 and a plurality of switches 14. The housing contains circuitry connected to the display 2 and switches 14 and a pressure transducer (not shown in FIG. 1). A conduit jack 16 is provided for connection to one end of a conduit 18, the other end of which is connected to a mouthpiece 20. The housing 10 has a power jack 22 for receiving 9-12 VDC from an AC power transformer 24. In the rear of the housing (not shown) a battery receptacle is provided for receiving five 1.2 volt AAA batteries.

Figure 2A:
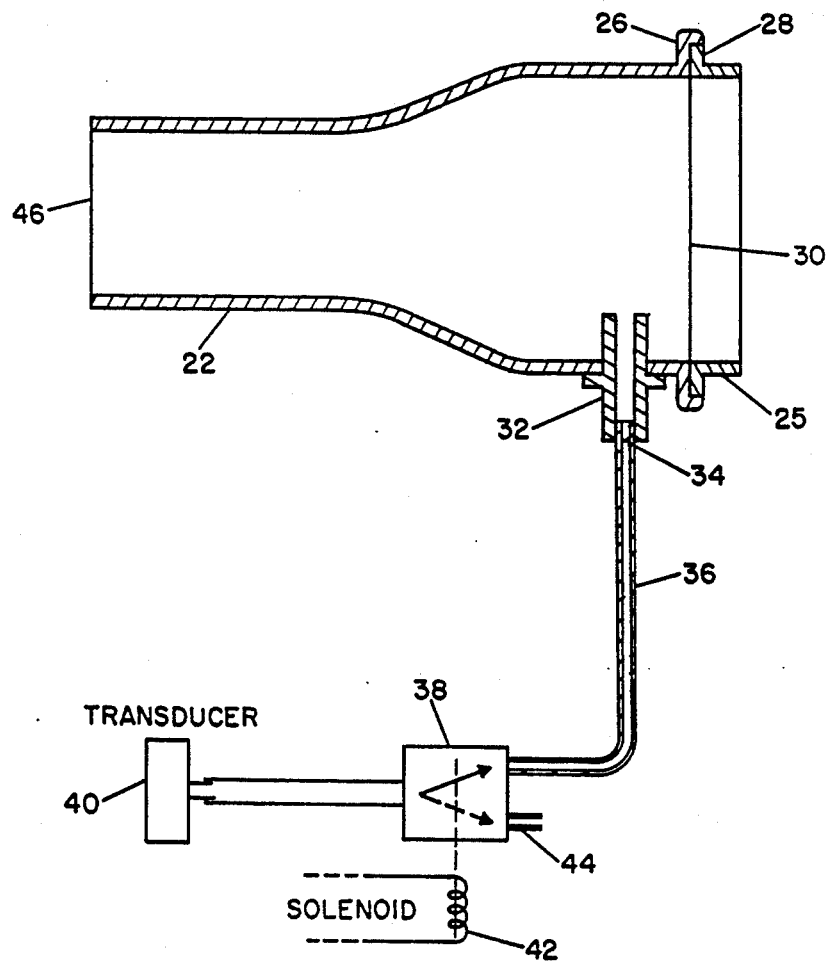
FIG. 2a is an elevation view, in partial cross section, of the mouthpiece, conduit, valve mechanism and transducer of the pulmonary function tester according to the invention.

Referring now to FIG. 2a, the mouthpiece 20 comprises an upstream section 22 and a downstream section 25 of plastic material, such as polystyrene, and which includes annular flanges 26 and 28, respectively. During construction, a woven polyester monofilament fabric resistance diaphragm 30, made by Tetko, Inc. under model number HD 7-21, is positioned between the two sections 22 and 25 and the sections are then joined by adhesive or ultrasonic bonding thereby holding the fabric in place. A tube 32 defines a port 34 for receiving a conduit or hose 36 to communicate with a three-way valve 38. The valve 38 is connected to pressure transducer 40 and is controlled by solenoid 42 to switch the transducer between connection to conduit 36 or to a vent port 44.

The mouthpiece 20 has at its end 46 a diameter of about 1.25 inches, which is conventional, because it allows this end 46 to fit in the mouth of a patient without permitting the patient to purse his lips. The mouthpiece cross sectional area widens as shown and has a diameter at the location of the fabric of about 2.0 inches.

The arrangement of the mouthpiece and the particular fabric specifications of diaphram 30, are selected so that the differential pressure across diaphram 30 due to the fabric's resistance does not impede the air flow greatly or cause an excessive back pressure. The pressure present at the transducer due to inhaling and/or exhaling into the mouthpiece end is predictable and repeatable in the flow range of interest.

The mouthpiece may also be replaced for each patient under test.

As will be further described the instrument detects when the flow rate is relatively low, on the order of less than 250 cc/sec, e.g., and then causes the solenoid to switch the three-way valve 38 to connect the transducer to atmosphere through port 44. An average of 3 samples of the transducer output is then stored as a zero-level sample since it corresponds to atmospheric pressure and zero flow rate. The total time that the transducer is vented through port 44 to atmosphere is relatively short, e.g. on the order of 0.1 sec or less, and the time between zero readings is relatively long, e.g. at least one second or more.

Figure 2B:
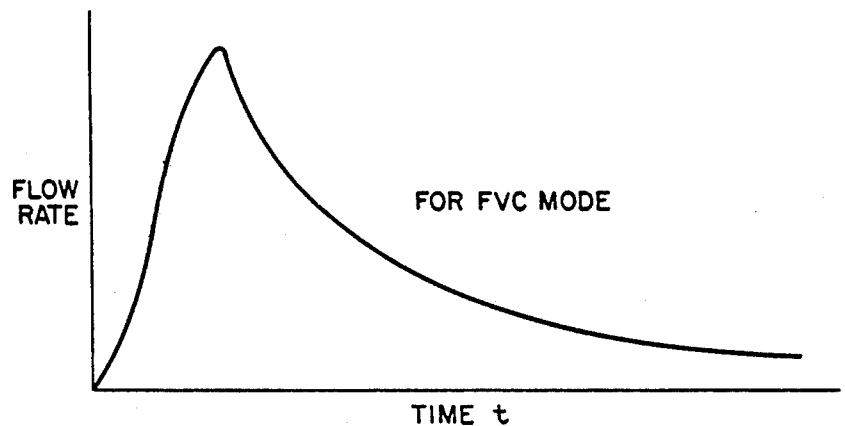
FIG. 2b is a plot of flow rate vs. time for the FVC mode.

In the Forced Vital Capacity (FVC) mode, the flow rate plotted vs. time looks like a curve shown in FIG. 2B, and the zero-level samples are taken after the flow rate drops below 250 cc/sec. In other modes, such as Resting Ventilation (RV), or Maximum Voluntary Ventilation (MVV), the zero-level samples are taken at the flow rate minimums when a cessation of flow rate is sensed (i.e. between inhalation and exhalation). Using a period of low flow rate to take a zero-level sample for calibration purposes minimizes volume measurement error.

A zero-level sample is also taken at the beginning of every test, and a check is made to insure that the zero-level has not drifted into an unusable range. A five-second-long period of sampler is checked for consistency which insures that the transducer has finished warming up and that there is not excessive electrical noise in the circuit. The valve remains activated during this time, thus ensuring that the transducer is exposed to ambient air pressure rather than potentially false pressures due to movement at the mouthpiece. The value of the most recent zero-level sample is stored in memory and is the value subtracted from subsequent pressure measurement samples to arrive at the calibrated transducer reading.

As will be described, the output of the transducer is a voltage which is amplified, converted by a voltage-to-frequency converter (V/F) to a pulse train having a frequency from 100 Hz to about 330 KHZ, such frequency being directly proportional to transducer pressure, and hence, flow rate, and then calibrated by subtracting the most recent zero-level value. The pulses from the V/F output are then processed using one of two sampling techniques (volume sampling for FVC mode and time sampling for modes other than FVC, as will be described). The sample values are actually directly proportional to volume per unit time in time sampling, and time per unit volume in volume sampling. The samples are then stored and used to calculate parameters of interest in the selected mode. The results are then stored and available for display.

In the case of FVC mode, up to 15 sets of test results can be selectively stored. In addition, the set of "best values", as described by the American Thoracic Society, is determined from the sets of test results, and can be displayed. Further, predicted values (according to patient's height, age, sex and race) can be calculated according to one of two commonly-accepted set of values (Knudson or ITS), and percent of predicted values displayed for any single test or for the set of "best values".

By converting the transducer output analog voltage into a frequency signal using a V/F converter, and then by counting the pulses from the V/F converter output, an analog to digital conversion is performed using hardware components. This V/F method of doing analog to digital conversion is preferable over a standard 12 bit CMOS A/D converter because of significantly lower cost, fewer pin connections on the circuit board (8 pins for V/F vs. 24 pins for A/D converter), and better noise rejection. The noise rejection factor is important because of the noise due to the high movement sensitivity of the pressure transducer which causes noise resulting from the physical movement of the instrument while being held in the hand, and the "ringing" of the pressure waveform (from overshoot and damped oscillations) due to the conduit or tubing connecting the transducer and mouthpiece. This integrating type A/D arrangement has much greater noise rejection characteristics than a standard successive-approximation type because much of the noise appearing as peaks and valleys disappears during the conversion process. The conversion times are long enough to average out the small peaks and valleys, but not too long as to miss detection of small variations of importance. Volume sampling is possible only with an integrating-type A/D, and is an advantage for respiratory measurements over successive-approximation methods, particularly because the resolution of the measurement increases as flow decreases. Software integration is prone to rounding errors, is slow and/or expensive due to increased precision in calculations and may sample at a time where a noise spike appears, thus increasing error.

Figure 3:
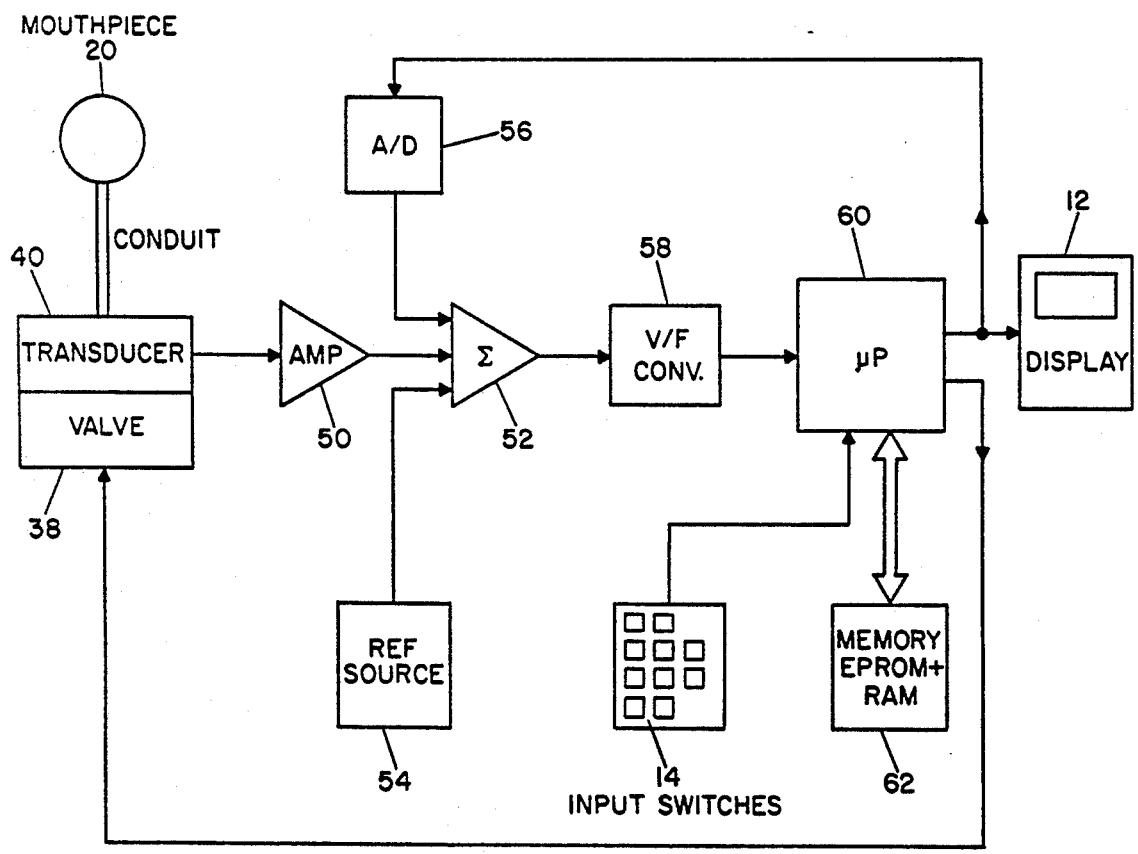
FIG. 3 is a simplified block diagram of the electrical components of the pulmonary function tester according to the invention.

FIG. 3 shows, in simplified block diagram form, the pulmonary function tester according to the invention.

The tester comprises a mouthpiece connected to a transducer. The transducer 40 detects pressure changes which are proportional to the flow rate in the mouthpiece 20. The output of the transducer is fed to amplifier 50, whose output is fed to summer 52. The summer 52 also receives a reference signal from reference source 54, which in the preferred embodiment is on the order of 1.2 volts. The summer 52 also receives, from analog-to-digital converter (ADC) 56 a baseline (zero flow) offset signal on the order of 0 volts to −1.2 volts, depending upon the particular calibration needed to zero the transducer, as will be described below. The summer 52 produces a voltage signal which is provided to voltage-to frequency converter (V/F) 58 which outputs a frequency signal ranging from about 0 to 300–330 KHZ and proportional to the magnitude voltage input thereto. The output of the V/F converter 58 is provided to an appropriate input of microprocessor 60, which samples the output of the V/F converter using one of two methods, ("time" or "volume"), as will be described below. The samples are stored in memory 62 for a later use in computing various parameters depending upon the particular pulmonary function being tested, as selected by input switches 14. The microprocessor 60 then computes one or more parameters for the particular pulmonary function being tested and displays the result on display.

The program for controlling the microprocessor 60 is stored in the EPROM memory section of memory 62, and a source code listing of such a program is provided by way of appendix hereto. A RAM section of memory 62 stores the samples of the output from the V/F converter 58 using a sampling method determined by the particular pulmonary function mode being tested.

The pulmonary function tester according to the invention provides four different testing modes: a Forced Vital Capacity (FVC) mode, a Negative Inspiratory Force (NIF) mode, a Maximum Voluntary Ventilation (MVV) mode and a Resting Ventilation (RV) mode.

In the FVC mode the subject should first inhale to maximum lung capacity, and then exhale as hard and as fast as possible through the provided mouthpiece. When in this mode, the sampling technique of the microprocessor of the output from the V/F converter is a "volume" sampling. According to this technique, the microprocessor counts the time required to achieve 10 milliliters in volume to the closest microsecond (0.001 sec), and the time values are stored as samples in RAM memory. The maximum V/F output is approximately 330 KHZ, and the zero level is set to approximately 16.5 KHZ. These values result in 256 V/F pulses being equal to 10 milliliters (0.4% volume accuracy). The conversion speed varies from 775 microseconds at 12 liters/second to 15 milliseconds at 0 liters/second (0 level). The conversion resolution in volume sampling varies from about 9 bits (0.2%) at 12 liters/second to 14 bits (0.006%) at flows less than approximately 150 millimeters/second. The 14 bit upper limit is due to the selected crystal tolerance, and is also about at the circuit noise level.

The arrangement provides for a high resolution at low flow rates which is ideal for FVC measurements that depend on accurate beginning/of/test and end/of/test determinations, where the flow is very low. Additionally, most of the flow encountered during an FVC process is in the lower range, where measurement resolution is 11 to 14 bits, as well as the conversion times being longer (longer conversion times mean better noise rejection).

From the stored samples, the following parameters are computed: 1) Forced Vital Capacity (FVC) in liters, 2) the Forced Expiratory Volume in one second (FEV1), expressed in liters, 3) the FEV,/FVC ratio in percent, 4) the peak flow rate in liters/second, 5) the Forced Expiratory Flow 5% 75% (FEF25-75 or MMFR) expressed in liters/second and 6) Extrapolated Volume (VOLextr %) expressed as a percentage of FVC. By pressing the "SEQ" button in sequence, the test parameters will be displayed on the display. The tester will retain all of the above set of test values (15 sets total) in memory until the FVC mode is exited or power is turned off.

In the RV, NIF and MVV modes, the microprocessor samples in accordance with a "time" sampling process wherein the number of pulses from the V/F converter is counted in a time interval of 0.010 seconds and that value is stored in RAM memory as a sample. During time sampling, resolution remains constant throughout the flow range, approximately 11 bits.

In the RV mode the subject should undertake normal breathing into the mouthpiece provided according to the invention. Measurement ceases after exactly one minute. The microprocessor will then compute from the data samples stored the parameters of 1) respiratory rate expressed in breaths/minutes, 2) tidal volume expressed. in volume/breath, and 3) minute volume expressed in volume/minute. All three parameters are displayed on a breath-by-breath basis, as well as the average of the latest 4 breaths.

In the NIF mode, the subject should inhale as hard as possible through the special adaptor, which is sealed at one end. This causes a negative pressure build-up inside the adaptor. The microprocessor then computes and displays according to the data samples stored the parameters of 1) the most negative pressure achieved in units of ($-$cm $H_2O$), and 2) a graphic display of negative pressure in the form of a 32-element bargraph.

In the MVV mode, the subject should breath as hard and fast as possible for a 15 second interval. A microprocessor will then compute from the data samples stored the parameters of 1) flow rate expressed in liters/second and 2) volume expressed in volume/breath.

Figure 4A:
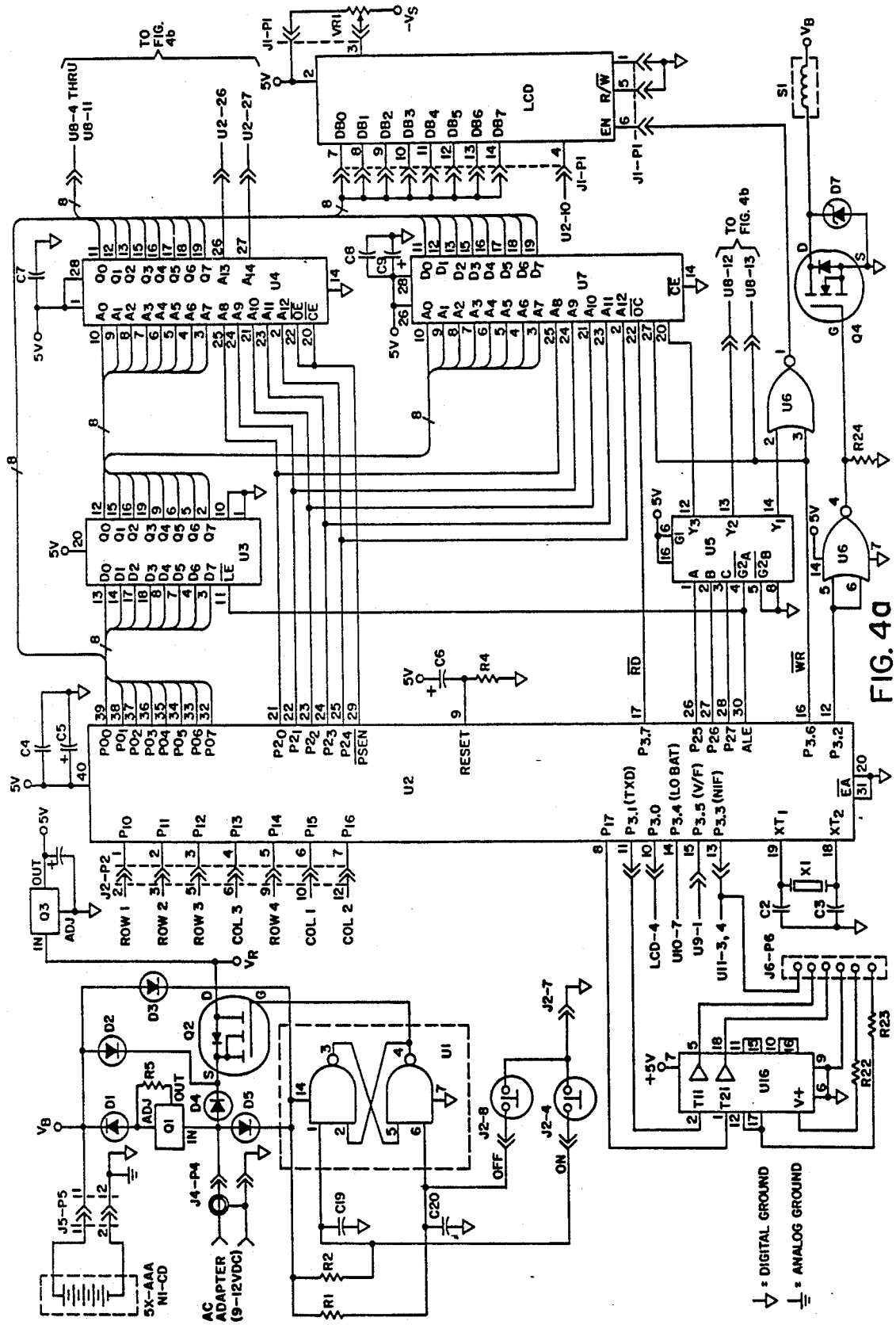
FIGS. 4a and 4b are detailed electrical schematics of the components shown in FIG. 3.
Figure 4B:
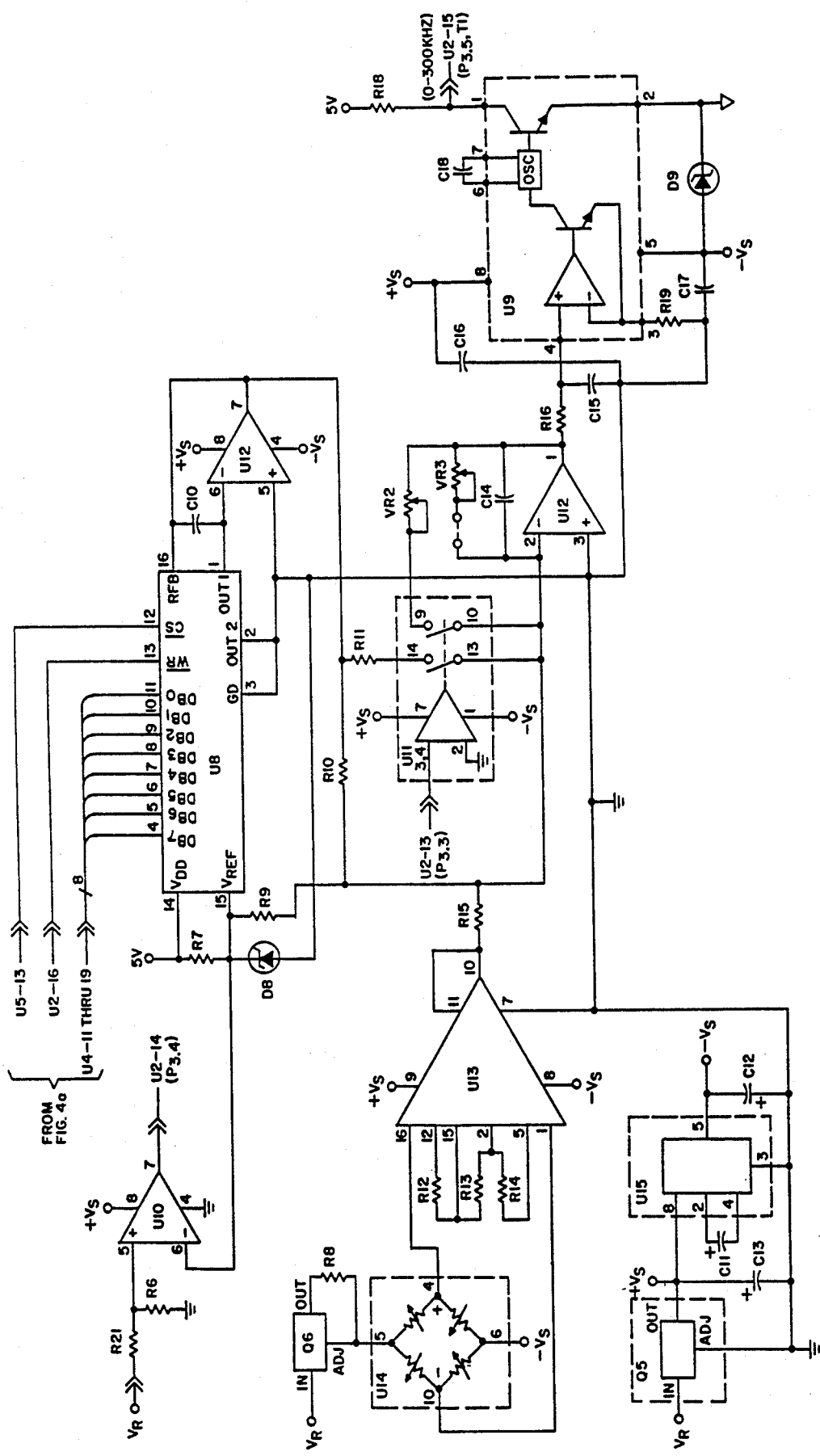

FIGS. 4a and 4b show, in more detail than FIG. 3, the electrical circuitry according to the invention. Referring to FIG. 4a, in the upper left hand corner is the power source interface which comprises a jack for connection to 5 NI-CAD AAA batteries. A battery charging circuit is also provided by way of IC Q1 and Q2, diodes D1, D2, D3, D4 and D5 and resistor R5. A five volt voltage regulator is provided by IC Q3, the input of which is Vr. This circuitry is also connected to an on/off latch provided by IC U1 which is further connected to ON and OFF switches as shown.

A microprocessor IC U2 is provided with connections as shown. The microprocessor is connected to rows and columns of momentary contact switches 14 (mode selection switches RV, FVC, NIF and MVV; operation START, STOP switches, CLEAR switch, RECALL switch, PRED (predicted values) switch, up and down arrow switches and ENTER switch in a conventional manner. These switches enable an operator to select various measurement and operating modes of the machine and the like. The microprocessor is connected to an output latch U3 as shown and a 32K byte EPROM IC chip U4. RAM memory is provided by way of IC chip U7 which is an 8K by 8 bit memory device. Also connected to the microprocessor, EPROM and RAM is an LCD module for display of the operating parameters measured by the device. An address decoder IC U5 decodes the addresses for the RAM, D/A converter (to be identified below) and the LCD display module. Additionally connected to the microprocessor U2 is a solenoid valve S1 through appropriate interface circuitry as shown.

In this FIG. 4a as well as in FIG. 4b, various connection points have been shown by way of identifying which IC and pins a particular line is to be connected to. Further, a Table at the end of the specification is provided to identify the particular values and model numbers for the circuit elements.

Referring now to FIG. 4b, a pressure transducer U14 is shown connected to a positive voltage supply regulator Q6 and a negative voltage supply −VS. The positive and negative outputs of the transducer are connected to an instrumentation amplifier U13 which provides a gain of approximately 30 (G=30). Shown below the transducer are a positive voltage supply regulator Q5 and a negative voltage supply U15. The instrumentation amplifier U13 has its output connected through resistor R15 to a summer U12A. Also connected to the input of the summer U12A is a voltage reference provided at the positive side of diode D8 through resistor R9, and the output of D/A converter U8 through its output amplifier U12B and through output resistor circuitry whose value varies depending upon whether the mode is NIF, or non-NIF (i.e. FVC, RV or MVV).

The D/A converter receives from microprocessor U4 an 8-bit byte which is used to create the offset "zero level". This is used for dynamic calibration of the device as will be described below. When the 8-bit byte is 0000 0000, the D/A output voltage is zero volts, and when 1111 1111, the output voltage is −1.2 volts. The output of the D/A converter is provided to IC chip U128 which at its output provides an analog signal within the range of −1.2 volts to 0 volts. The "zero level" offset value appearing at the output of U12B is then used to either partially or totally offset the reference voltage of 1.2 volts on the positive side of the diode D8 and the zero pressure voltage from the transducer. Summer U12A thus sums its 3 inputs through three respective summing resistors: (1) the transducer output through resistor R15, (2) the Vref voltage from the positive side of diode D8 through resistor R9, and (3) the calibration signal at the output of U12B through resistor R10 alone for non-NIF modes, and the parallel combination of R10 and R11 for the NIF mode.

When the NIF mode is selected, the microprocessor outputs an appropriate signal to U11 which is a switching device which closes its switches to connect terminals 13 and 14 together, and 9 and 10 together. When the switches are so closed, the summing resistors for the calibration signal outputted at U12 are provided by the parallel combination of resistors R10 and R11. When the switch also connects pins 9 and 10 of the switching device U11, the feedback loop for the summer U12A places resistor VR3 in parallel with VR2, instead of the sole resistor VR3 for non-NIF modes. The switching device U11 thus effects the gain in the summer U12A to provide an overall gain G between instrumentation amplifier U13 and summer U12A of about 300 (G=30 for U13 and G=10 for U12) in the non-NIF modes. For the NIF modes, U12A has a gain of about 1 to provide an overall gain of about 30 for U13 and U12.

The output of summer U12A is provided to a voltage to frequency converter (V/F) which provides an output signal in the form of a pulse train having a frequency of between 0 to 300-330 KHZ in dependence and in proportion to the magnitude of the analog voltage appearing at its input pin 4 thereto. Thus, the frequency of the pulse train appearing at its output is directly proportional to the pressure sensed by the pressure transducer U14, which in turn is a predictable function of the air flow through the mouthpiece. The output of the V/F converter is fed to an input of the microprocessor which then counts or times the pulses and stores samples, using either the time sampling method or the volume sampling method described elsewhere herein.

A unique aspect of the present invention is its ability to perform dynamic calibration. During operation in one of its measurement modes, the microprocessor, through its control program stored in EPROM, senses when the transducer output appearing at the output of V/F converter U9 drops below a selected level. When this occurs, the microprocessor energizes the solenoid valve S1 which, as shown in FIG. 2a, switches the three-way valve from a position connecting the transducer to the mouthpiece, to a position connecting the transducer to atmosphere for a brief time period which is less than 0.1 second. The program then stores in memory the most recent up-to-date numerical representation of the transducer zero level. In this way, measurement accuracy is improved during periods of zero drift, which can occur during the brief period of measurement, and which is an unavoidable consequence (due to warm up, temperature drifts, mechanical bonding of the sensor chip, and both electrical and mechanical hysteresis effects on the silicon sensor chip) of using piezoresistive technology. The value of the "zero level" stored in memory during the calibration sampling period is a digital value which is provided to the input to the D/A converter U8.

Figure 5D:
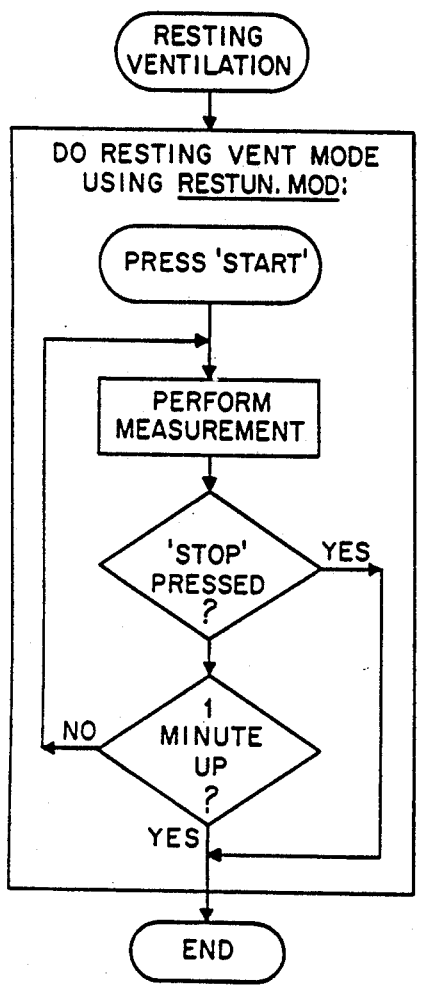

Referring now to FIGS. 5a-5l, flowcharts of the source program listing provided on microfiche will now be described. In FIG. 5a, after the system is turned on by depressing "ON" switch, the display provides a sign on message and determines whether any of the four mode switches of FVC, MVV, RV or NIF, or PRED (Predicted Values) or RECALL switches have been pressed. If so, the program proceeds to the respective module corresponding to the depressed switch. If not, the program waits until one of these six switches are depressed. FIGS. 5b-5g are flowcharts of the six respective modules shown in 5a.

In the CALIBRATION module of FIG. 5b, the program determines whether any mode has been run since the device has been turned on. If it has, the calibration mode cannot be selected. Otherwise a calibration can be performed by simultaneous pressing of two particular switches, and is done using the module CALIB. MOD. In this module, the digital-to-analog converter is checked, and pressure calibration for NIF modes and non-NIF modes can be performed, along with other internal circuitry tests. The module is then exited.

In FIG. 5c, the FVC mode includes a number of modules. In the FVC.MOD module, which is the executive module for the FVC mode, the FVCMEA and FVCALC modules are called, all the results of these modules are stored and displayed, and the best effort for the particular patient is calculated. When called by the FVC.MOD module, the FVCMEA module performs actual measurement of the FVC waveforms, and stores A/D samples for use by FVCALC. The FVCALC calculates six parameters from data samples which were stored by the FVCMEA module. The six parameters had been described above. The PRED or predict module displays predicted values according to one of two selectable, widely-accepted data bases using sex, age, height and race data corresponding to the patient that had been entered by the operator. In this way, the actual results of the patient's tests can be compared with target values. If "Best" is pressed, the best values for all tests done since the FVC mode was entered are displayed. The "best" values are selected according to American Thoracic Society recommendations. The program remains in the FVC mode until another mode is selected.

In FIG. 5d, in the RESTING VENTILATION mode, the module performs measurements on the obtained data until the stop switch is depressed or until one minute has elapsed. The module is exited when another mode is selected.

Figure 5E:
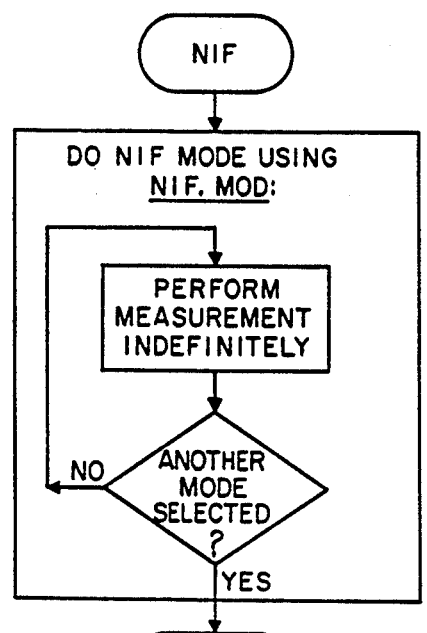

In FIG. 5e, for the NIF mode, the module performs measurements for this mode indefinitely until another mode is selected, whereupon the module is exited.

Figure 5F:
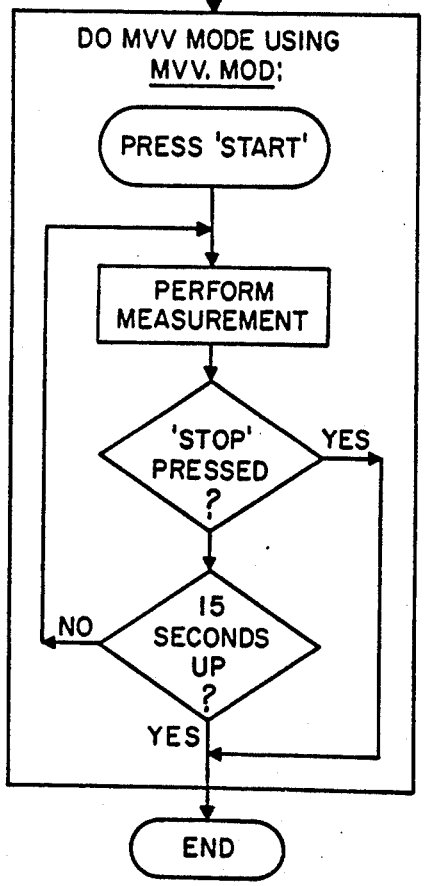

In FIG. 5f, the module performs measurements upon first of either the stop button being depressed or the elapse of 15 seconds. The module is exited when another mode is selected.

In the PREDICT module of FIG. 5g, if this module is entered from any mode other than the FVC mode, the module will display patient data if it has already been entered, and allowing changes to this data if desired. Alternatively, it will prompt the user to enter the patient data if such data has not yet been entered. If this mode was entered from other than the FVC mode, no predicted values will be displayed. Only if this mode was entered from the FVC module will the predicted values be displayed.

FIGS. 5h-5l, show various utility software modules which are generally used by all of the above-described modes. In the ATZ or auto zero module of FIG. 5h, the module first opens the solenoid valve or vents to atmosphere, then checks to determine whether the battery voltage level is low and if so, an appropriate message is displayed. The zero level is adjusted and monitored via time sampling in the manner described above. Electrical noise and zero level drift is then checked and if the count has varied or drifted more than a certain amount within a specified amount of time, the zero level is again monitored for the specific amount of time determined. Once the count drift is determined to be below a certain level, this final level is then stored as the value used for subsequent calibration. This ATZ module is used by all modes except the CALIB module, which has its own auto zeroing routine.

Figure 5J:
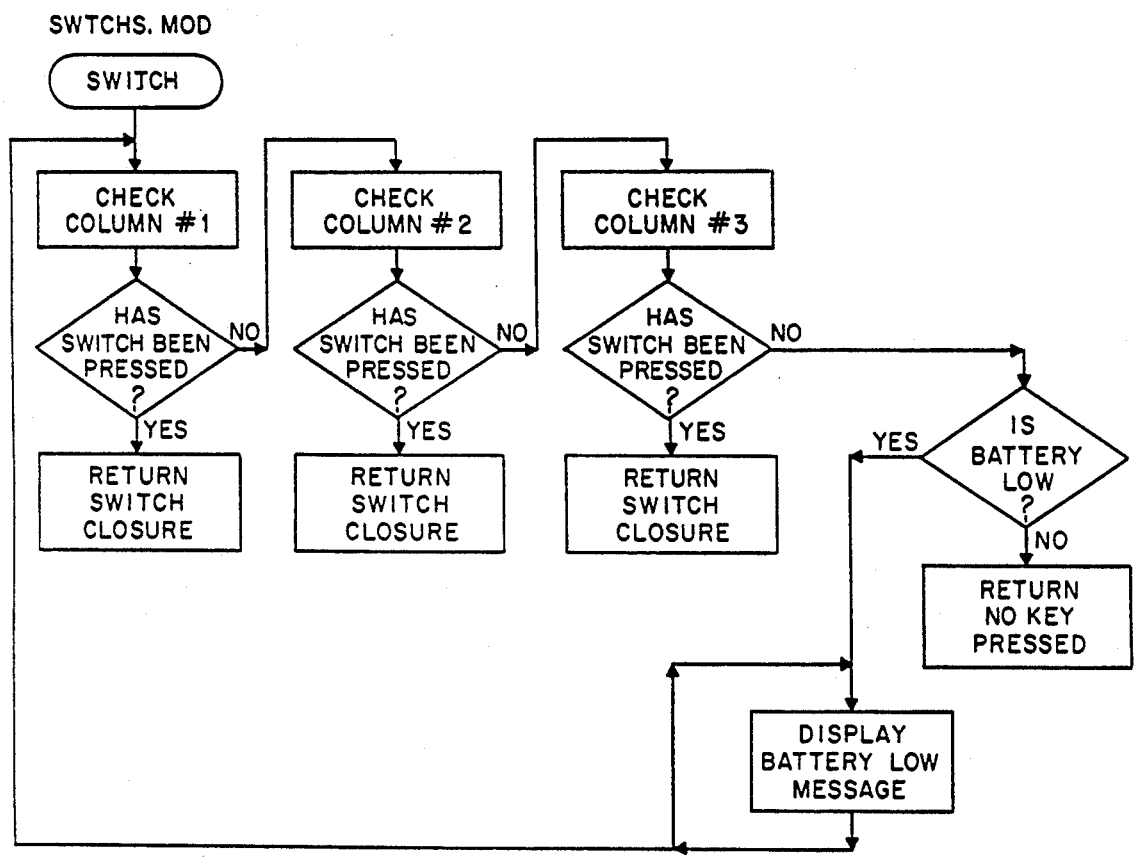
Figure 5K:
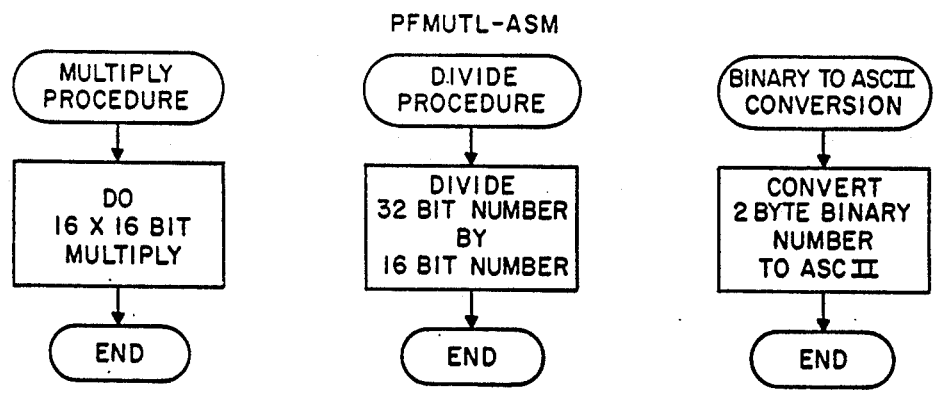
Figure 5I:
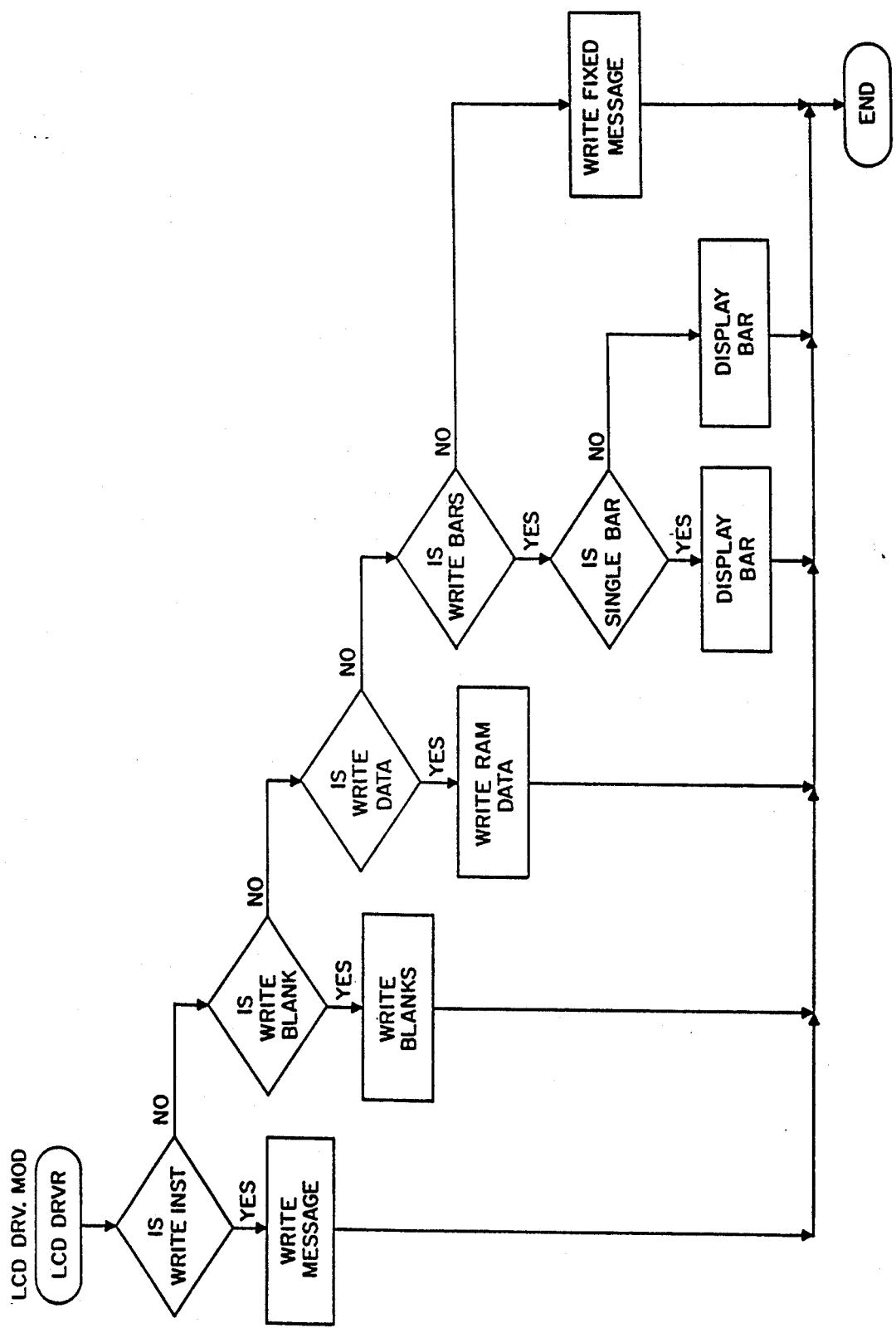

In the LCD DRIVER module of FIG. 5i, the module displays characters, bars and values in RAM memory and clears all or part of the LCD module. This module is usable by all of the modes.

In the SWITCH module of FIG. 5j, a switch check routine is provided which checks for switch closures by first activating a column of switches, and then finding the particular row. The module also checks for low battery voltage. This module returns to the module which called it with the selected switch identified.

In FIG. 5k, basic arithmetic assembly language routines are provided including 16 by 16 bit multiplication, 32 bit by 16 bit divide, and 16 bit binary to ASCII coded decimal.

Lastly, in FIG. 5l, the INTERRUPT module controls all analog-to-digital sampling, generates calibrating message during auto zeroing, and generates and displays a real time clock for resting vent (RV) and MVV modes.

As indicated above, the source code listing of the program for the microprocessor is provided by way of the attached appendix.

While a preferred embodiment has been shown and described, it is to be understood that numerous variations and modifications may be effected without departing from the true spirit and scope of the concept of the invention. The invention is limited only by way of the following claims.

TABLE

| | | | |
|---|---|---|---|
| R1 | 10K | C1 | 220 UF - 10 V |
| R2 | 10K | C2 | 30 PF |
| R3 | 3.6K | C3 | 30 PF |
| R4 | 8.2K | C4 | 0.1 UF |
| R5 | 68 | C5 | 2.2 UF (TA) |
| R6 | 10K 1% | C6 | 10 UF |
| R7 | 7.5K | C7 | 0.1 UF |
| R8 | 866 1% | C8 | 0.1 UF |
| R9 | 82K 5% | C9 | 2.2 UF (TA) |
| R10 | 39K 5% | C10 | 330 PF |
| R11 | 866 1% | C11 | 10 UF |
| R12 | 20K 1% | C12 | 47 UF (TA) |
| R13 | 1.37K 1% | C13 | 47 UF (TA) |
| R14 | 20K 1% | C14 | 0.01 UF (POL) |
| R15 | 4.75K 1% | C15 | 0.1 UF |
| R16 | 16K | C16 | 2.2 UF (TA) |
| R17 | 10 | C17 | 0.1UF |
| R18 | 3.6K | C18 | 270 PF (POL-2.5%) |
| R19 | 750 1% | C19 | 0.1 UF |
| R20 | 10 | C20 | 0.1 UF |
| R21 | 28.7K 1% | | |
| R22 | 3K 5% | | |
| R23 | 3K 5% | | |
| R24 | 100K 5% | | |
| VR1 | 20K | | |
| VR2 | 5K | | |
| VR3 | 50K | | |
| D1 | IN4001 | U1 | ¼ 40011B |
| D2 | IN4001 | U2 | 80C31 |
| D3 | IN914 | U3 | 74C373 |
| D4 | IN4001 | U4 | 27256 |
| D5 | IN914 | U5 | 74HC138 |
| D6 | SD103 | U6A | ¼ 74HC02 |
| D7 | IN5248B (18 V) | U6B | ¼ 74HC02 |
| D8 | AD589JH or LM385Z-1.2 | U7 | CDM6264 |
| D9 | SD103 | U8 | AD7524 |
| | | U9 | AD654 |
| | | U10 | ½ ICL7621 |
| | | U11 | AD7512DI |
| | | U12A | ½ LT1013 |
| 12B | | U12B | ½ LT1013 |
| | | U13 | AD625 |
| | | U14 | ICS Model |
| | | U15 | ILC7660 |
| | | U16 | MAX 233CPP |
| | | LCD | Hitachi |
| Q1 | LM041/Optrex DMC 16433 | | |
| Q1 | LM317L | S1 | solenoid |
| Q2 | IRFD9123 | X1 | 12.0000 MHZ |
| Q3 | 2950CZ-5.0 | | |
| Q4 | IRFD123 | | |
| Q5 | 2950CZ-5.0 | | |
| Q6 | LM317L | | |

I claim:
1. A pulmonary function tester for measurement of a patient's pulmonary function comprising:
   a) means for sensing ambient atmospheric pressure;
   b) means for sensing the pressure created by a patient's pulmonary function after said means for sensing ambient atmospheric pressure has sensed ambient atmospheric pressure;
   c) means for sensing ambient atmospheric pressure after said means for sensing the pressure created by a patient's pulmonary function has sensed the pres- sure created by a patient's pulmonary function; and, d) means for calibrating the pressure sensed by said means for sensing the pressure created by a patient's pulmonary function in view of a difference between the pressure sensed by said means for sensing ambient pressure prior to sensing the pressure created by a patient's pulmonary function and the pressure sensed by said means for sensing ambient atmospheric pressure after sensing the pressure created by a patient's pulmonary function.

2. The pulmonary function tester of claim 1 wherein said means for calibrating includes means for storing an indicator of each of the following: the pressure sensed by said means for sensing ambient pressure prior to sensing the pressure created by a patient's pulmonary function; the pressure sensed by said means for sensing the pressure created by a patient's pulmonary function; and, the pressure sensed by said means for sensing ambient atmospheric pressure after sensing the pressure created by a patient's pulmonary function.

3. The pulmonary function tester of claim 1 wherein said means for sensing ambient pressure prior to sensing the pressure created by a patient's pulmonary function and said means for sensing ambient atmospheric pressure after sensing the pressure created by a patient's pulmonary function are the same means.

4. The pulmonary function tester of claim 3 wherein said means for sensing ambient pressure prior to sensing the pressure created by a patient's pulmonary function and said means for sensing ambient atmospheric pressure after sensing the pressure created by a patient's pulmonary function is a pressure transducer.

5. The pulmonary function tester of claim 1 wherein said means for sensing ambient pressure prior to sensing the pressure created by a patient's pulmonary function and said means for sensing ambient atmospheric pressure after sensing the pressure created by a patient's pulmonary function are distinct means from said means for sensing the pressure created by a patient's pulmonary function.

6. The pulmonary function tester of claim 5 wherein said means for sensing ambient pressure prior to sensing the pressure created by a patient's pulmonary function and said means for sensing ambient atmospheric pressure after sensing the pressure created by a patient's pulmonary function is a pressure transducer.

7. The pulmonary function tester of claim 6 wherein said means for sensing the pressure created by a patient's pulmonary function is a pressure transducer.

8. The pulmonary function tester of claim 5 wherein said means for sensing the pressure created by a patient's pulmonary function is a pressure transducer.

9. The pulmonary function tester of claim 1 wherein said means for sensing ambient atmospheric pressure prior to sensing the pressure created by a patient's pulmonary function, said means for sensing the pressure created by a patient's pulmonary function, and said means for sensing ambient atmospheric pressure after sensing the pressure created by a patient's pulmonary function are the same means.

10. The pulmonary function tester of claim 9 further comprising means for alternately connecting said same means to ambient atmosphere and to said patient's pulmonary tract.

11. The pulmonary function tester of claim 10 wherein said means for alternately connecting comprises a valve means.

12. A pulmonary function tester for measurement of a patient's pulmonary function comprising:

a) means for sensing a pressure level presented to said means for sensing and for producing an output signal indicative of the sensed pressure level;

b) means for connecting said means for sensing to a patient's pulmonary tract and for storing a corresponding said output signal representative of the sensed pressure produced by the patient's pulmonary tract;

c) means for calibrating said output signal from said means for sensing when said means for sensing is connected to a patient's pulmonary tract comprising:

i) means for connecting said means for sensing to ambient atmosphere for a time interval sufficient for said means for sensing to accurately sense an initial pressure level prior to sensing the pressure produced by the patient's pulmonary tract and for storing the corresponding said output signal;

ii) means for connecting said means for sensing to the ambient atmosphere for a time interval sufficient for said means for sensing to accurately sense a final pressure level after sensing the pressure produced by the patient's pulmonary tract and for storing the corresponding said output signal; and iii) means for calculating the difference between the levels of said output signals when said means for connecting said means for sensing a pressure level is connected to the ambient atmosphere to sense an initial pressure level and when said means for connecting said means for sensing a pressure level is connected to the ambient atmosphere to sense a final pressure level, and for adjusting said output signal representative of the sensed pressure produced by the patient's pulmonary tract in view of the calculated difference.

13. A method of measurement of a patient's pulmonary function comprising the steps of:

a) sensing ambient atmospheric pressure;

b) sensing the pressure created by a patient's pulmonary function after sensing ambient atmospheric pressure;

c) sensing ambient atmospheric pressure after sensing the pressure created by a patient's pulmonary function; and, d) calibrating the pressure sensed in step b) in view of a difference between the pressure sensed in step a) and in step c).

14. The method of claim 13 wherein said step of calibrating includes the step of storing an indicator of each of the following; the pressure sensed in step a); the pressure sensed in step b); and, the pressure sensed in step c).

15. The method of claim 13 wherein steps a) and c) are performed by the same means.

16. The method of claim 15 wherein the means for performing steps a) and c) is a pressure transducer.

17. The method of claim 13 wherein steps a) and c) are performed by the same means and step b) is performed by a means distinct from said means for performing steps a) and c).

18. The method of claim 17 wherein step a) and c) are performed by a pressure transducer.

19. The method of claim 18 wherein said means for performing step b) is a pressure transducer distinct from said pressure transducer for performing steps a) and c).

20. The method of claim 17 wherein said means for performing step b) is a pressure transducer.

21. The method of claim 13 wherein steps a), b) and c) are performed by the same means.

22. The method of claim 21 further comprising the step of alternately connecting said same means for performing steps a) and b) and step c) to ambient atmosphere and to a patient's pulmonary tract, respectively.

23. The method of claim 22 wherein said step of alternately connecting is performed by a valve.

24. A method for measuring a patient's pulmonary function comprising the steps of:
 a) sensing a first ambient pressure level for a time interval sufficient to accurately sense an initial ambient pressure level and storing an indicator of the sensed first ambient pressure level;
 b) sensing a patient's pulmonary tract pressure level for a time interval sufficient to accurately sense the patient's pulmonary tract pressure level and storing an indicator of the patient's pulmonary tract pressure level;
 c) sensing a second ambient pressure level for a time interval sufficient to accurately sense a final ambient pressure level and storing an indicator of the sensed final ambient pressure level; and,
 d) calculating the difference between the stored indicators of the initial and final ambient pressure level and adjusting the indicator of the patient's pulmonary tract pressure level in view of the calculated difference.

* * * * *